(12) United States Patent
Buser et al.

(10) Patent No.: US 8,961,548 B2
(45) Date of Patent: Feb. 24, 2015

(54) SAFETY STOP TROCHAR DEVICE AND SYSTEM

(75) Inventors: John Buser, San Diego, CA (US); Patrick Diesfeld, Ventura, CA (US)

(73) Assignee: Laprostop, LLC, San Diego, CA (US)

( * ) Notice: Subject to any disclaimer, the term of this patent is extended or adjusted under 35 U.S.C. 154(b) by 394 days.

(21) Appl. No.: 12/249,439

(22) Filed: Oct. 10, 2008

(65) Prior Publication Data

US 2009/0030443 A1 Jan. 29, 2009

Related U.S. Application Data

(63) Continuation-in-part of application No. 12/022,704, filed on Jan. 30, 2008, now abandoned, which is a continuation-in-part of application No. 11/383,896, filed on May 17, 2006, now abandoned, which is a continuation-in-part of application No. 11/146,655, filed on Jun. 6, 2005, now abandoned.

(51) Int. Cl.
| | |
|---|---|
| *A61M 5/32* | (2006.01) |
| *A61B 17/34* | (2006.01) |
| *A61B 19/00* | (2006.01) |
| *A61M 25/02* | (2006.01) |
| *A61B 17/00* | (2006.01) |

(52) U.S. Cl.
CPC ......... *A61B 17/3423* (2013.01); *A61B 17/3496* (2013.01); *A61B 19/5202* (2013.01); *A61B 2017/3445* (2013.01); *A61B 2017/347* (2013.01); *A61B 2017/3492* (2013.01); *A61B 2019/5206* (2013.01); *A61B 2019/521* (2013.01); *A61M 25/02* (2013.01); *A61B 2017/00283* (2013.01)
USPC ....... 606/174; 604/177; 604/178; 604/164.01

(58) Field of Classification Search
USPC .................. 606/108, 172, 184, 185; 604/162, 604/164.01, 164.08, 174, 177, 178, 264; 128/202.27
See application file for complete search history.

(56) References Cited

U.S. PATENT DOCUMENTS

| | | | | | |
|---|---|---|---|---|---|
| 2,820,457 | A | * | 1/1958 | Phillips | 128/200.26 |
| 3,765,420 | A | * | 10/1973 | Felczak | 604/117 |
| 4,258,722 | A | * | 3/1981 | Sessions et al. | 600/566 |
| 4,781,694 | A | * | 11/1988 | Branemark et al. | 604/175 |
| 4,809,694 | A | * | 3/1989 | Ferrara | 606/130 |
| 4,878,698 | A | * | 11/1989 | Gilchrist | 285/342 |
| 4,959,055 | A | * | 9/1990 | Hillyer | 604/179 |
| 5,020,534 | A | * | 6/1991 | Pell et al. | 128/207.15 |
| 5,121,949 | A | * | 6/1992 | Reese | 285/255 |
| 5,217,441 | A | * | 6/1993 | Shichman | 604/536 |
| 5,251,616 | A | * | 10/1993 | Desch | 128/200.26 |
| 5,257,973 | A | * | 11/1993 | Villasuso | 604/539 |
| 5,335,946 | A | * | 8/1994 | Dent et al. | 285/243 |

(Continued)

OTHER PUBLICATIONS

European Search Report Jul. 23, 2013.

*Primary Examiner* — Dianne Dornbusch
(74) *Attorney, Agent, or Firm* — Steins & Associates, P.C.

(57) ABSTRACT

A safety-stop trochar device and system for use with a trochar and surgical accessory devices. The device and system has a base into which an insert seats over which a cap secures to the base and also secures a previously inserted trochar or drainage device or smoke evacuator or surgical accessory such as an obturator and illumination device. Flexible extension wings on the base have distal suture apertures or an adhesive on the bottom of the base, or both, for securing the base to a patient. U-shaped extensions on the cap facilitate cap placement or removal onto or from the base.

12 Claims, 8 Drawing Sheets

(56) References Cited

U.S. PATENT DOCUMENTS

| | | | | |
|---|---|---|---|---|
| 5,364,367 A | * | 11/1994 | Banks et al. | 604/174 |
| 5,366,446 A | * | 11/1994 | Tal et al. | 604/180 |
| 5,372,583 A | * | 12/1994 | Roberts et al. | 604/506 |
| 5,380,302 A | | 1/1995 | Orth | |
| 5,382,240 A | * | 1/1995 | Lam | 604/177 |
| 5,562,688 A | * | 10/1996 | Riza | 606/148 |
| 5,716,326 A | * | 2/1998 | Dannan | 600/204 |
| 5,792,112 A | * | 8/1998 | Hart et al. | 604/164.01 |
| 5,897,531 A | * | 4/1999 | Amirana | 604/180 |
| 5,993,437 A | * | 11/1999 | Raoz | 604/536 |
| 6,039,725 A | * | 3/2000 | Moenning et al. | 606/1 |
| 6,328,748 B1 | * | 12/2001 | Hennig | 606/130 |
| 6,464,690 B1 | * | 10/2002 | Castaneda et al. | 606/1 |
| 6,491,699 B1 | * | 12/2002 | Henderson et al. | 606/130 |
| 6,554,802 B1 | * | 4/2003 | Pearson et al. | 604/177 |
| 6,752,812 B1 | * | 6/2004 | Truwit | 606/130 |
| 6,902,569 B2 | * | 6/2005 | Parmer et al. | 606/108 |
| 7,144,388 B2 | * | 12/2006 | Crawford | 604/192 |
| 7,455,328 B2 | * | 11/2008 | Chelchowski et al. | 285/323 |
| 7,695,480 B2 | * | 4/2010 | Solar et al. | 606/130 |
| 7,722,571 B2 | * | 5/2010 | Bierman et al. | 604/180 |
| 2002/0049451 A1 | * | 4/2002 | Parmer et al. | 606/108 |
| 2006/0008332 A1 | * | 1/2006 | Greenberg et al. | 408/202 |
| 2006/0293702 A1 | | 12/2006 | Buser et al. | |

* cited by examiner

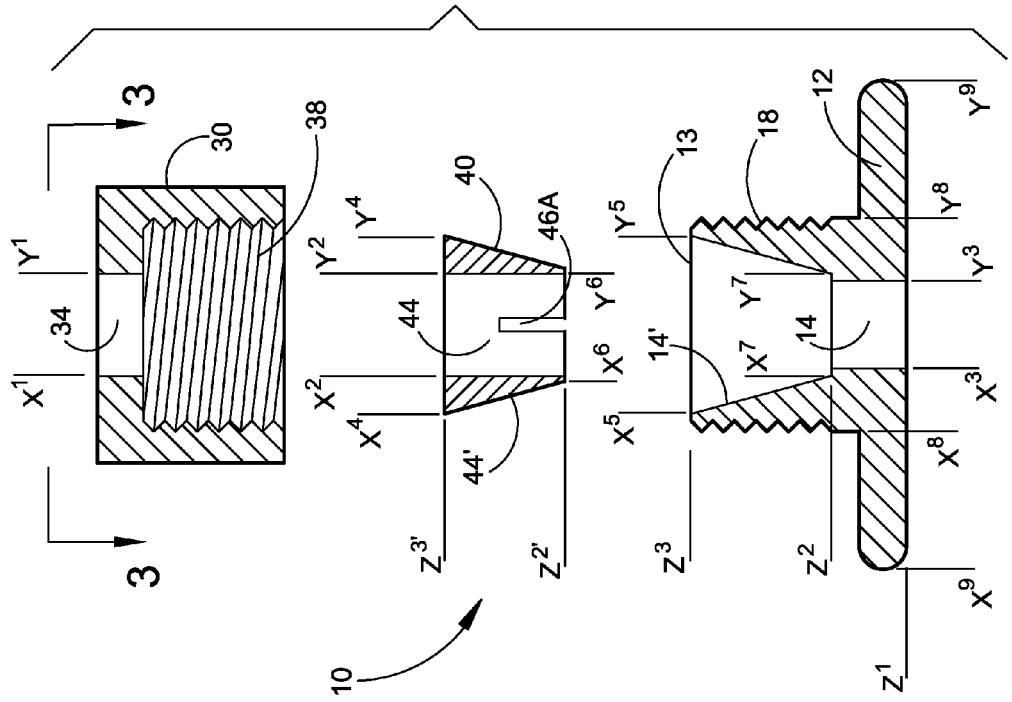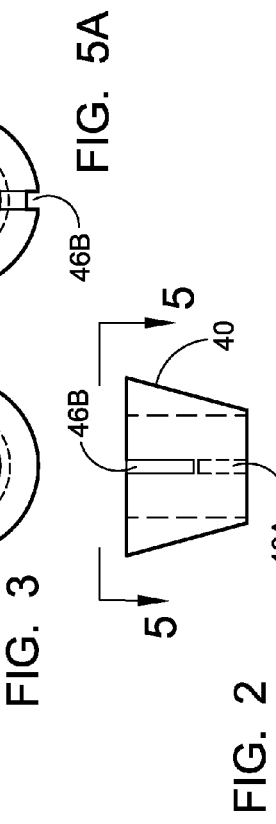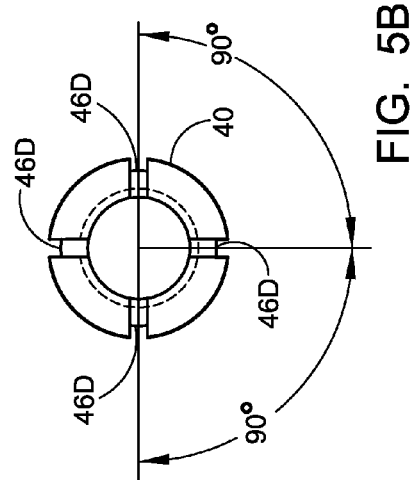

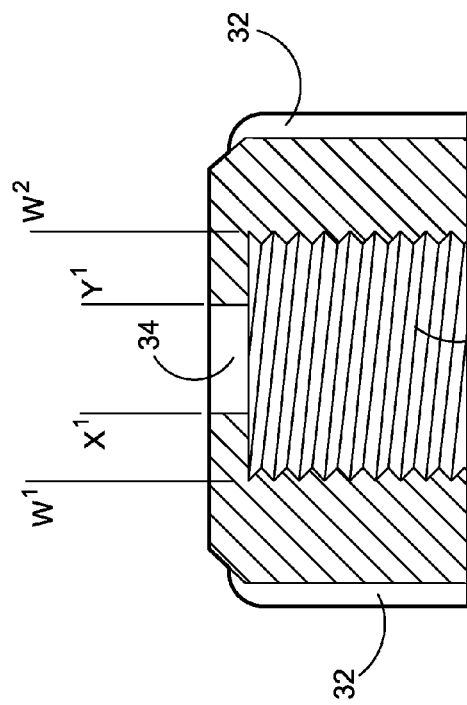
FIG. 6
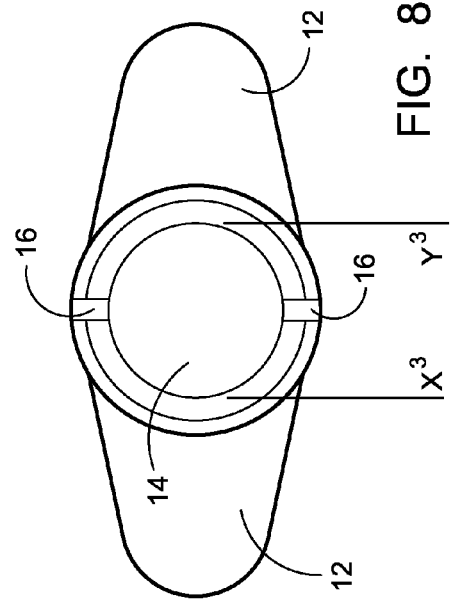
FIG. 7
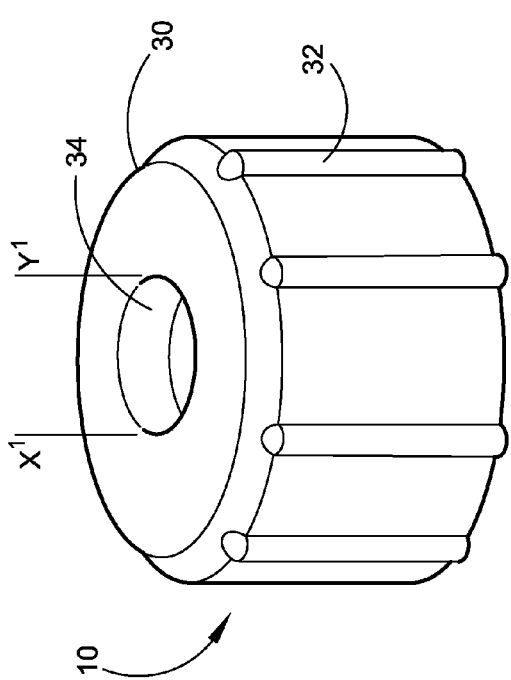
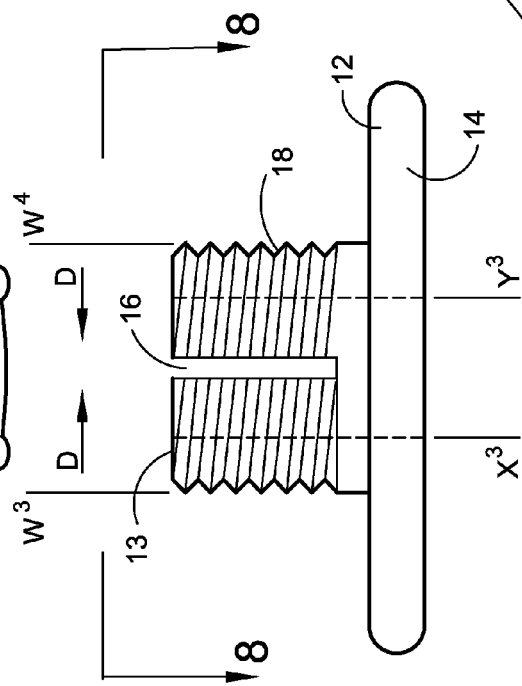
FIG. 8

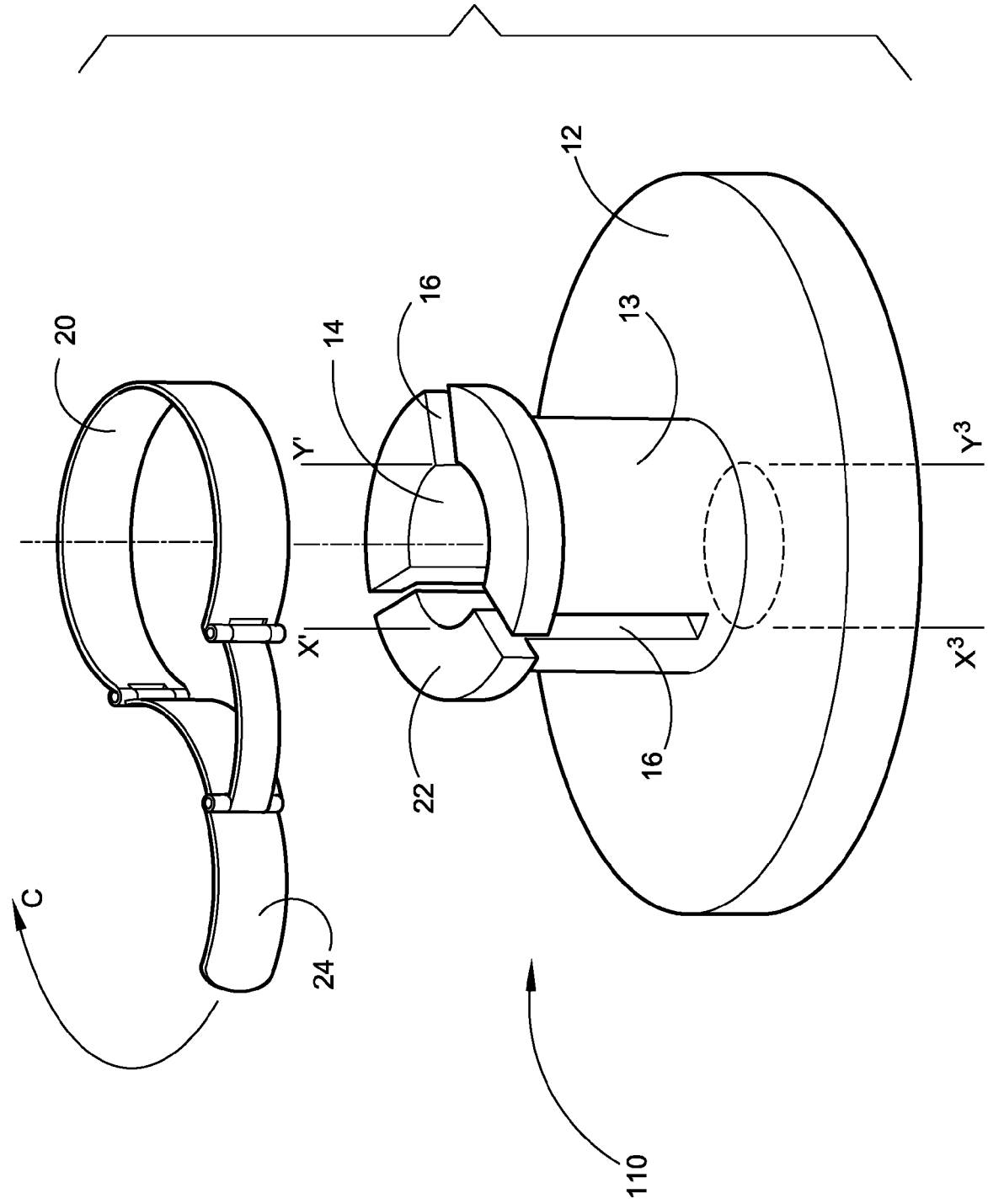

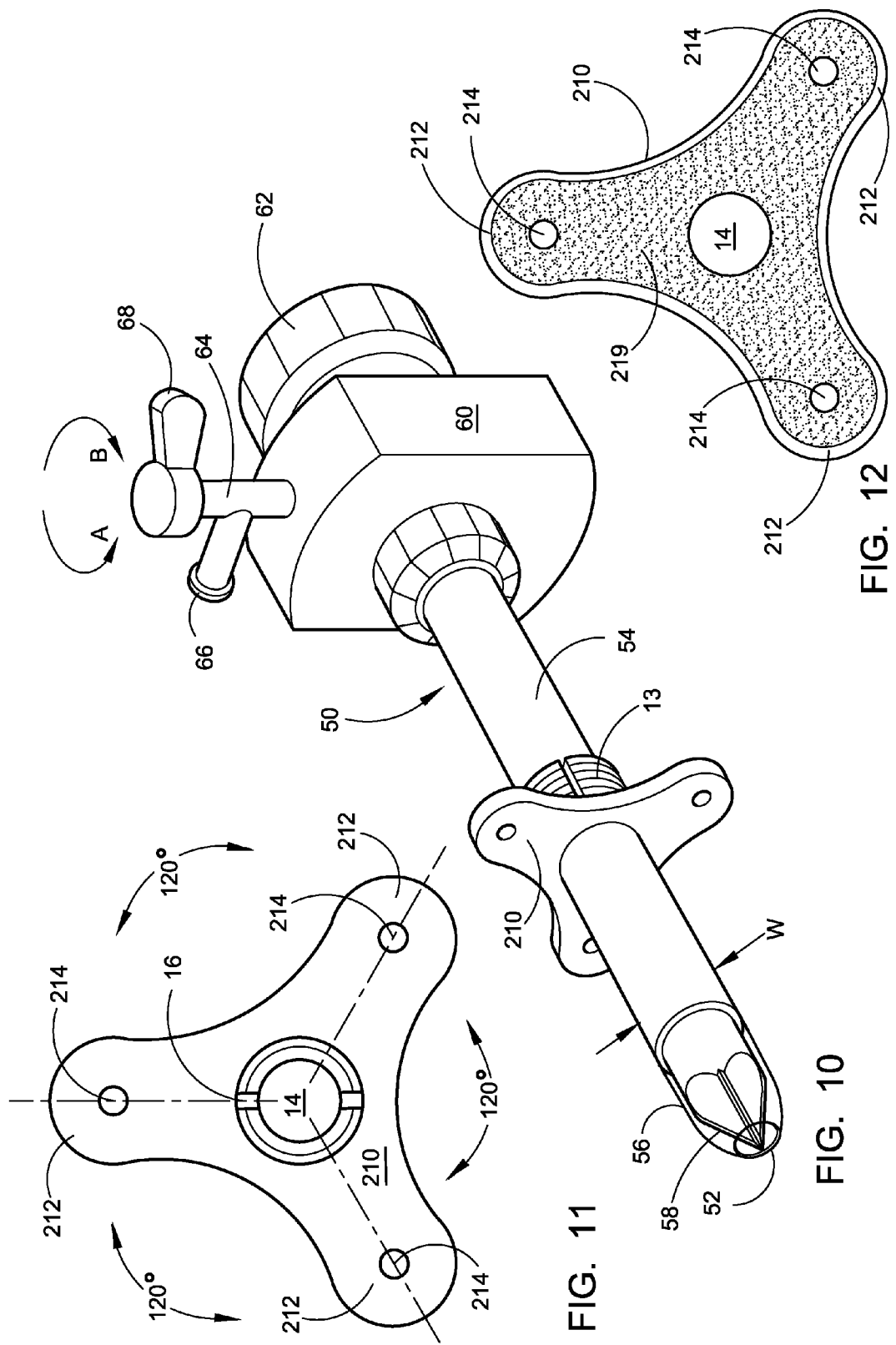

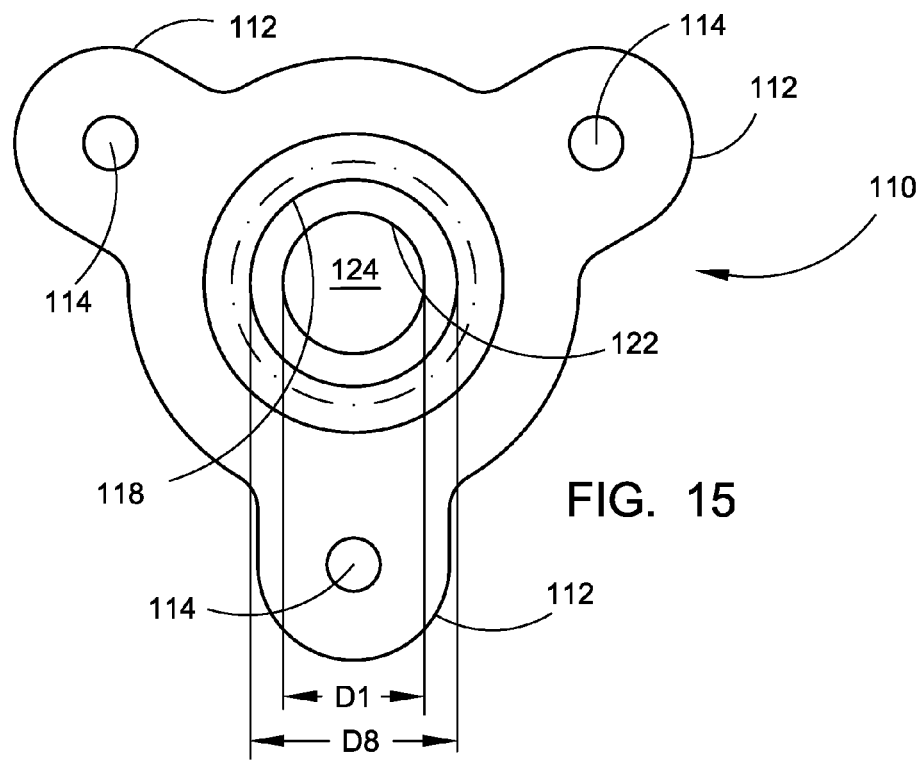
FIG. 15
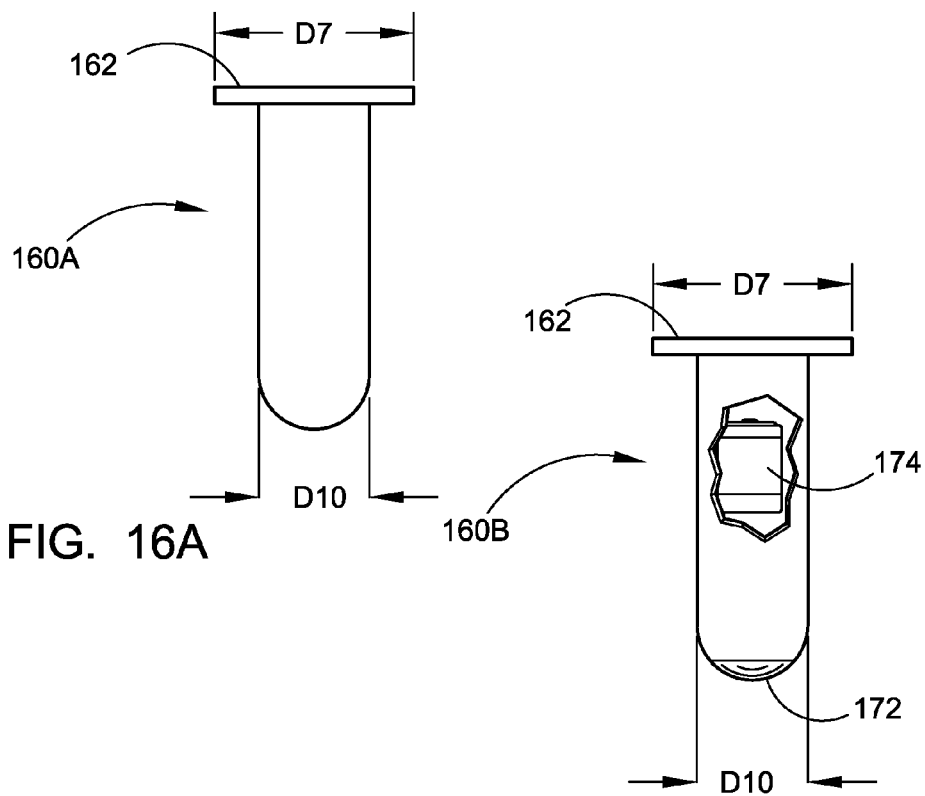
FIG. 16A
FIG. 16B

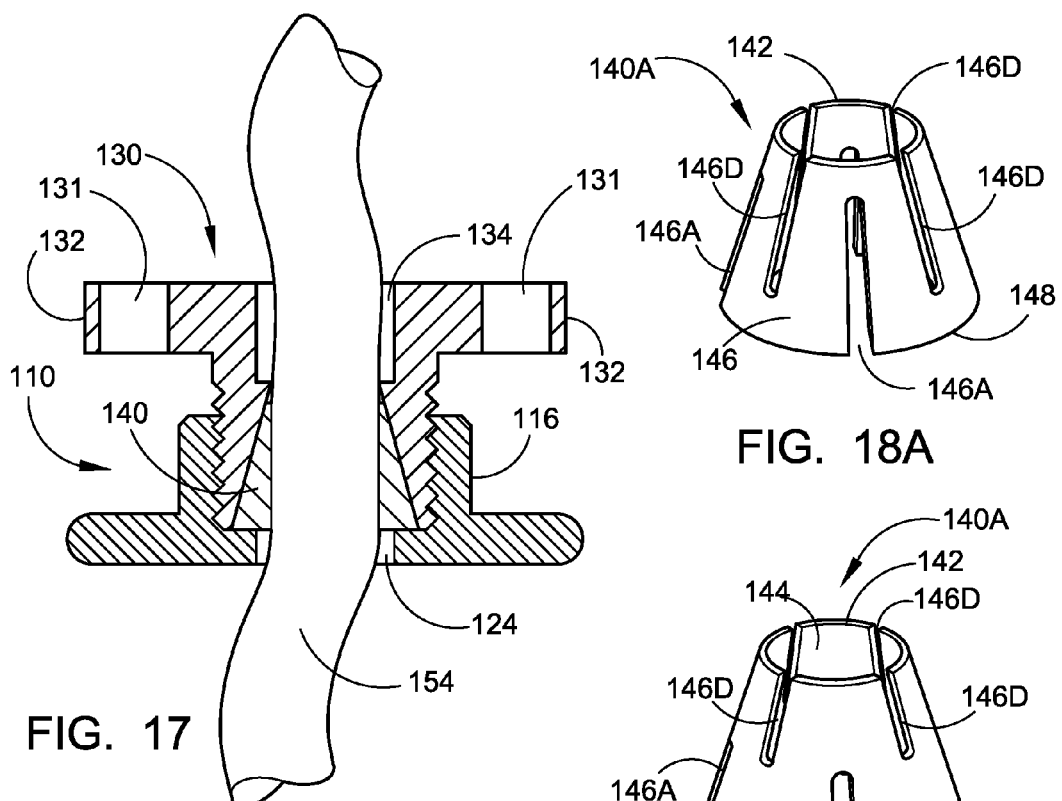
FIG. 17
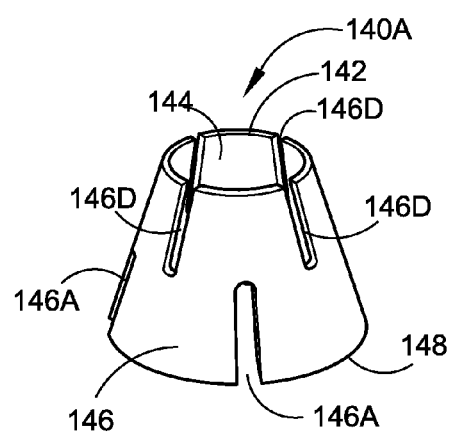
FIG. 18A
FIG. 18B
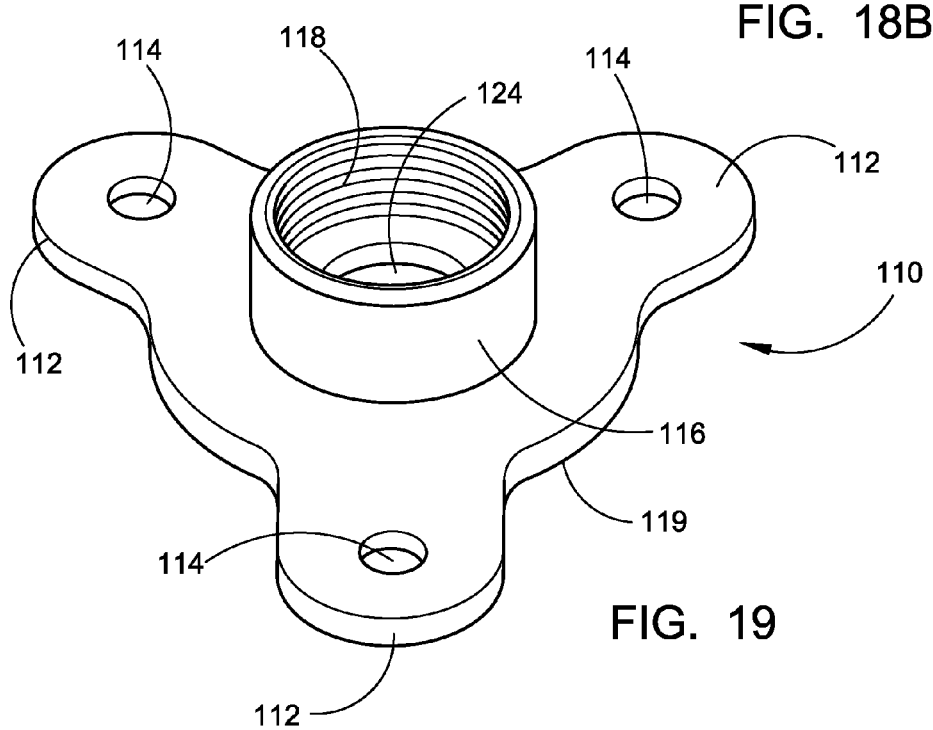
FIG. 19

SAFETY STOP TROCHAR DEVICE AND SYSTEM

CROSS REFERENCES TO RELATED APPLICATIONS

This application is a continuation-in-part of our application Ser. No. 12/022,704, filed on Jan. 30, 2008 now abandoned, which is a continuation-in-part application of my application Ser. No. 11/383,896, filed on May 17, 2006 now abandoned, which is a continuation-in-part application of my application Ser. No. 11/146,655, filed on Jun. 6, 2005 now abandoned.

STATEMENT REGARDING FEDERALLY-SPONSORED RESEARCH OR DEVELOPMENT

Not applicable

BACKGROUND

This safety-stop trochar device and system relates to an improvement in safety features for trochar assemblies [also referred to as trochar], and more particularly to a safety-stop, attachable to a trochar, registerable on a trochar, used on a trochar to permit puncture-movement of the trochar only to a pre-determined and pre-set depth, and interchangeability and concurrent or separate use of individual components therewith. These components include, but are not limited to, a drainage tube, a smoke evacuator, an obturator, and an illumination device each of which are adapted to be held securely in place during the course of a surgical procedure and thereafter as necessary or desired.

A trochar is sharp-pointed surgical instrument basically comprised of a stylet [the sharp cutting blades] and a cannula [a small tube for insertion into a body cavity or into a duct or vessel; also referred to herein as trochar tube or a sleeve] and is typically utilized to puncture a body cavity. The stylet is removably housed in the cannula and after the body cavity is punctured, the stylet is removed leaving the cannula in place and in communication with the body cavity whereby endoscopic, and similar, instruments can then be inserted through the cannula and into the body cavity.

Specific forms of minimally invasive surgical procedures include endoscopic and laparoscopic surgery which typically involve using small incisions and optical instrumentation being inserted into the body cavity. Endoscopy refers to video-assisted surgery that is performed through several small incisions rather than a single large incision. Laparoscopy is endoscopy that is done in the abdominal cavity.

The primary instrument used for the incisions necessary in these procedures is the trochar. The use of the trochar for these procedures greatly reduces the amount of cutting required in the course of surgery and, concomitantly, reduction of stress to the body. Reduction of stress to the body generally leads to faster recoveries and lower medical costs. Great care, however, must be exercised when performing such body cavity punctures with the trochar as the trochar blades are 'surgically' sharp and the exertion of manual force is required for the blades to pierce and go through the skin and abdominal wall of the patient.

A primary purpose of our safety-stop trochar device and system is to prevent the sharp trochar blades from accidentally being inserted too deeply. The inherent act of inserting the trochar and attempting to place it where desired requires applying a great deal of initial force down toward the deep anatomic structures, without being able to visualize them, then by sensing a loss of resistance, discontinuing the thrust.

All of this is generally done within a fraction of a second. Patient tissue-variability, in thickness and strength, further complicates the estimation of how much force is required, and for how long, to attain safe penetration.

Excess force, however minimal, or unforeseen factors within the body cavity could lead to piercing or cutting internal organs or other internal structures which could lead to inadvertent and severe life-threatening surgical complications. It has been known that some surgeons extend and use their finger, placed along the sleeve of the trochar, as a makeshift stop. This is awkward, inaccurate, and dangerous.

Trochars manufactured with shielded tips covering the blades; i.e., a safety shield, provide some aid in preventing inadvertent second cuts. While shielded trochar systems vary in their design, all generally have a spring-loaded retractable shield that covers the cutting tip on the blades of the trochar. The shields are either retracted prior to placement of the trochar in the wound or automatically retract during the placement. Once the sharp tip of the trochar's blades penetrates an abdominal wall and enters the abdominal cavity, the spring-loaded safety shield automatically deploys, covering the cutting tip and locking in place.

Theoretically, this prevents or decreases the incidence of damage to the bowel and the major vessels. Injuries can still occur, however, if the trochar is not used properly, if there is a malfunction of the safety shield, or with the presence of bowel adhesions to the anterior abdominal wall. Even with this improvement to the trochar, insertion of the primary trochar blades still remains a blind procedure.

Laparoscopy is a very commonly performed procedure throughout the world. In the U.S. alone, some 6 million cases are performed annually. The total number of cases is growing, as more specialties (general surgery, urology, gynecology) convert procedures over to the laparoscopic approach. Notwithstanding the safety features developed over the years for the trochar, laparoscopy has a background serious complication rate of approximately three to five per 1,000, due to trochar placement. These include intestinal damage, bladder damage, and most seriously large blood vessel (vascular) injury. Of the vascular injuries, which stand at one to two per 1,000, approximately 23% will die.

The majority of serious injuries occur when the stylet of the trochar, with cannula attached, is inserted too deeply, damaging the deeper structures within the body. Only 5 cm. maximum length is necessary, to enter the peritoneal cavity at the umbilicus, the most common entry site. However, trochars are 12 to 15 cm. in length, as a one size-fits-all device. The deep structures, most significantly major blood vessels, can be damaged at 7 to 10 cm, depending on the size of the patient, the degree of gas insufflation raising the abdominal wall, and the angle of thrust executed by the health-care provider.

Our safety-stop trochar device and system will function to reduce injuries and deaths to patients undergoing laparoscopic surgery. It will aid the health-care provider during the surgical procedure after one or more trochar incisions for internal surgery are made by:

a. applying a smoke evacuator to yet another of our safety-stop trochar device and system to remove smoke from the cavity which, in many laser and electro-surgical procedures, generate smoke and thereby obstructs the surgeon's vision;

b. applying a drainage tube to another of our safety-stop trochar devices and systems to effect drainage of fluids from the peritoneal cavity for post-operative evacuation of fluids;

c. applying a obturator to any one of our safety-stop trochar devices and systems after completion of surgery to thereby leave an incision unhealed and permit access into the cavity for viewing of post-operative results without the need to make another trochar incision or to force entry into the cavity from a closed and partially healed prior incision;

d. applying an illumination device to one of our safety-stop trochar device and system and into the cavity upon which surgery is being performed to provide much need full lighting of the peritoneal cavity to the surgeon;

e. inclusion of an adhesive on the underside of the base; and f. addition of U-shaped extensions on the cap to facilitate securing to the base.

During Laparoscopic surgery the surgeon is often called upon to use electro-surgical instruments for cutting and/or cauterizing inside the peritoneal cavity. Because these instruments are essentially burning the flesh, they create a great deal of smoke that limits the already limited visibility a surgeon has when viewing the procedure through a laparoscope. Now, a shortened smoke evacuator cannula can be placed through a trochar and secured by our safety-stop device/trochar system [base 110, insert 140, and cap 130] in place. This would be like maintaining a vacuum hood over a range while cooking, which can be activated periodically. Current technology typically requires a smoke evacuator to be grasped, fed through the trochar, activated, removed from the cannula, and replaced where it won't fall off the surgical field. This process is repeated numerous times throughout the surgical procedure.

This entire new system to include a smoke evacuator is designed to allow the surgeon a hands-free way to evacuate smoke from the peritoneal cavity during surgery using the safety-stop trochar device/system as a platform. Anything that can be done to improve this view has the potential of shortening the surgical procedure, saving operating room time (saving money) and saving lives. The current method of evacuating smoke from the peritoneal cavity is to have an additional set of hands holding the tube in a spot dictated by the surgeon. The smoke evacuator of our present inventive system will eliminate the need for this costly person.

The addition of a drain holder [in conjunction with an insert of approximately ±3 MM) was also fashioned into this new system. Many surgeries entail placement of drains, usually hollow Jackson-Pratt type drains, to remove accumulating blood or pus or serious drainage over the critical one to four day post-operative period. These drains generally are sutured to the skin, which is NOT ideal when infection and pus are present, as is often the case. Our safety-stop device and entire new system, with the adhesive base, can secure the drains more optimally and provides a secure base to which a drainage tube can be attached. It requires only that the safety-stop trochar device/system be provided with one 1-2 additional inserts to fit the common sizes of drainage tubes.

The current method of attaching a drainage tube is insecure and often un-sterile and can be accidentally pulled out. Many complications occur because sutures have to be placed in an area of the body that may be contaminated by pus. For aesthetic reasons, many patients find suture scars undesirable. The Adhesive back of the safety-stop trochar device/system flange provides a secure platform for inserting the drainage tube and eliminates the need for stitches when holding it in place. Our original safety-stop device, in itself is a unique device and the drainage tube holder is designed to supplement it, as a complete system in a way that makes it even more unique in it's design and overall function.

When performing laparoscopic surgeries, up to five trochars can be used to make incisions in the lap for the laparoscope or any of the surgical instruments. It is often desirable to have a "second look" within hours to days after the initial surgery is performed. The purpose of these second looks is to re-enter and check for correct healing, possible infections, proper drainage of the abdominal cavity and other post-operative complications. The current method of taking these second looks is re-enter one of the ports into the lap that were made during the initial surgery by removing the stitches that were used to close the incision.

This requires an un-stitching and mechanical re-opening of the incision which may have already partially healed. Surgeons have indicated a need to have an easier way to re-enter the original incision made by the trochar for a second look.

This sterile obturator, placed through a laparoscopic port incision, and secured by a safety-stop trochar device/system, allows maintaining a laparoscopic port. Indications may include expected re-operation in one to three days, or irrigation of an intra-abdominal or pelvic abscess. During the period between the initial surgery and the second look, the incision may begin to heal and is often partly closed when the surgeon removes the stitches.

The inclusion of an obturator in the present system provides a method by which an it can be inserted into the peritoneal cavity with relative ease and as unintrusively as possible. It can be made of any plastic, thermoplastic, rubber, metal, urethane or polymer and can be installed in less than a minute permitting easy entry for the surgeon to place a scope for a second look and obviates the need for stitching and un-stitching the incision which is partially healed. It does not impede performance of the remainder of the surgery.

When performing laparoscopic surgeries, the peritoneal cavity in insufflated with gas creating a balloon-like dome in the peritoneal cavity in which to operate. Currently lighting for laparoscopic surgery is quite rudimentary. Typically the surgeon dedicates one hand to pointing the light on a scope at a particular object he/she wishes to see. This is like shining a flashlight in an empty room and only seeing the desk or like entering a room with a flash light without full overhead lighting when it is preferable to turn on the overhead light and see everything.

The addition of an illumination device into the present safety-stop trochar device/system greatly facilitates the vision for a surgeon. The illumination device can be a short light, such as a LED light or any conventional fiber optic light, to illuminate the peritoneal cavity. This would be either placed through a short trochar, or passed through the surgical port site, after the trochar created the opening, and was removed. This could create greater, more uniform illumination of the surgical field, with all the associated benefits of accuracy, decreased surgeon fatigue and less shadowing. Also, the heavy fiber optic light cord could be eliminated, and a better laparoscope could evolve, which did not include a light channel running through it, which sacrifices camera lens space and capacity.

This illumination concept was primarily designed to allow the surgeon a hands free way to illuminate the entire peritoneal cavity through the use of a corded or battery powered light that uses the safety-stop trochar device/system as a platform.

These structures and features were not conceived and, therefore, not mentioned in our prior, above-referenced, patent applications. From use of our safe-stop device described in those prior patent applications, we have discovered additional needs which currently are not met by any prior art device or our co-pending prior patent applications.

As with our co-pending applications, our safety-stop trochar device and system can be made of any material though, for cost considerations, any form of plastic or, particularly for the base wings, pliant plastic is best suited. Furthermore it can, but need not, be disposable for further patient safety as a one-time use.

As in our co-pending patent application, the base of our safety-stop trochar device and system also has a plurality of wings [extensions] as a base support and at least one aperture adjacent to the ends of the wings. The purpose of this structure is to permit the user to secure the base to the patient by suturing the base to the patient through the apertures on the wings. This more effectively and efficiently secures the base to the patient thereby freeing up the user's hand by not requiring the user to steadily hold the base onto the patient without movement; a difficult position to maintain.

What our co-pending applications did not conceive until now was a less intrusive alternative to suturing; an adhesive substance on the bottom of the wings is included to thereby permit a user to merely clean a patient's skin and directly apply the base to the skin. The adhesive secures the base to the skin without need of suturing.

In a co-pending application, a flexible base was addressed and described which allows the correspondingly inserted trochar a full range of motion, restriction that a rigid base may impose. The flexible base, in combination with the addition of an adhesive base presents a more useful and adaptive device. Securing the safety-stop trochar device/system to the patient eliminates trochar dislodgement, which frequently occurs with instrument exchanges, and which frequently leads to loss of the CO2 gas which is holding up the anterior abdominal wall. This is a significant setback to surgical progress, and has some risk in addition to the inconvenience. The adhesive base allows another non-invasive option, in addition to suturing, to secure the safety-stop trochar device/system to the patient.

The wings may be comprised of any material but it has been found that if the wings are rigid, in use the wings tend to cause bruising to the patient. A thermoplastic material or a thermoplastic rubber material is best suited for the construction of the base and the wings. It has been found that wing pliability affords a user greater flexibility of placement of the safety-stop trochar device and system and minimize, if not eliminate, bruising a patient. Depending on where a trochar is to be used on a patient, angling of the safety-stop trochar device and system may be necessitated. The pliability of the base and wings, due to the materials of which they are composed, also facilitates placement, angling, and safe and more exacting use of the safety-stop trochar device and system and trochar attached to it.

The safety-stop trochar device and system also facilitates introduction of surgical instruments through the tube upstanding from the base without fear of excess movement by the user. The base, sutured to the patient or secured by the adhesive, holds fast, without movement, facilitating the procedures to follow.

Also in our co-pending patent applications it was not conceived, and consequently not described, of use of a wing-nut type concept for the cap with U-shaped protrusions extension outward from the cap; the protrusions being on opposite side of each other. Two such protrusions are ideal but three or four may also function well.

In our co-pending application, typically an external object, such as a wrench, is used to secure the cap to the base, thereby adding compression to the insert so as to secure the device onto the cannula of the trochar. Personal experience and anecdotal data gathered from other surgeons have led applicants to seek an alternative method of securing the safety-stop trochar device/system without the use of a wrench.

The foregoing has outlined some of the more pertinent objects of the safety-stop trochar device and system. These objects should be construed to be merely illustrative of some of the more prominent features and applications of the safety-stop trochar device and system. Many other beneficial results can be attained by applying the disclosed safety-stop trochar device and system in a different manner or by modifying the safety-stop trochar device and system within the scope of the disclosure.

Accordingly, other objects and a fuller understanding of the safety-stop trochar device and system may be had by referring to the summary of the safety-stop trochar device and system and the detailed description of the preferred embodiment in addition to the scope of the safety-stop trochar device and system defined by the claims taken in conjunction with the accompanying drawings.

SUMMARY

The above-noted problems, among others, are overcome by the safety-stop trochar device and system. Briefly stated, the safety-stop trochar device and system contemplates a complete system of component parts for use with a trochar where the main components of this system include a base, an insert, a cap, and several complimentary surgical components such as a drainage device, a smoke evacuator [each used in conjunction with the insert], an obturator, and an illumination device [each used without the insert]. The main components, when involved with laparoscopic surgery are used as a multi-purpose platform to assist the surgeon in six discreetly independent procedures that are common to laparoscopic surgeries: controlling depth of trochar insertion, stabilizing the trochar during instrument exchanges, providing a platform for eliminating smoke, providing a platform for eliminating accumulated liquids/fluids [such as blood, pus, or serious drainage] which poses a health hazard to a patient, providing a platform for maintaining a post-operative incision in a patient for later inspections, and providing a platform for illuminating the operating field.

The base, insert, and cap are attachable to the trochar tube to prevent inadvertent cuts being made to a patient. Three flexible extension wings on the base and associated adhesive on the bottom of the base permit the base to be secured to the patient without suturing the base to the patient. Apertures in the wings provide for a suturing option if deemed necessary or desired by the surgeon.

The cap has U-shaped extension on opposing sides of the cap wall to aid in attaching and threading the cap to the base. An opening through the cap from top to bottom consists of two distinct sections; an upper section which is perpendicular to the cap floor and a lower section which is angled downward and outward toward the cap floor. This configuration facilitates acceptance of the insert and its compression to thereby secure external objects within the insert bore.

The foregoing has outlined the more pertinent and important features of the safety-stop trochar device and system in order that the detailed description that follows may be better understood so the present contributions to the art may be more fully appreciated. Additional features of the safety-stop trochar device and system will be described hereinafter which form the subject of the claims. It should be appreciated by those skilled in the art that the conception and the disclosed specific embodiment may be readily utilized as a basis for modifying or designing other structures and methods for carrying out the same purposes of the safety-stop trochar device and system. It also should be realized by those skilled in the art that such equivalent constructions and methods do not depart from the spirit and scope of the safety-stop trochar device and system as set forth in the appended claims.

BRIEF DESCRIPTION OF THE DRAWINGS

For a fuller understanding of the nature and objects of the safety-stop trochar device and system, reference should be had to the following detailed description taken in conjunction with the accompanying drawings in which:

FIG. 2 is an elevation, cross-sectional, exploded view of a first embodiment of the safety-stop device described in a co-pending application.

FIG. 3 is a plan view of the cap component of the safety-stop device described in a co-pending application as taken on line 3-3 of FIG. 2.

FIG. 4 is a cross-section view of the opposite side, rotated 180°, of the insert 40 as illustrated in FIG. 2.

FIG. 5A is a plan view of the insert device described in a co-pending application as taken on line 5-5 of FIG. 4.

FIG. 5B is a plan view of the insert device showing in more detail the four upper slots.

FIG. 6 is an elevation view of a second embodiment of the safety-stop device described in a co-pending application.

FIG. 7 is a cross-section elevation view of the cap illustrated in FIG. 6.

FIG. 8 is a plan view of a first embodiment of the base of the safety-stop device described in a co-pending application as taken on line 8-8 of FIG. 6.

FIG. 9 is a perspective exploded view of a third embodiment of the safety-stop device described in a co-pending application.

FIG. 10 is perspective view of a typical trochar assembly with a second embodiment of the base of the safety-stop device described in a co-pending application.

FIG. 11 is a plan view of the second embodiment of the base of the safety-stop device described in a co-pending application as taken on line 8-8 of FIG. 8.

FIG. 12 is a bottom plan view of the base of FIG. 11 illustrating the adhesive on the bottom.

FIG. 15 is a top plan view of the base.

FIGS. 16A and 16B are detailed views of an obturator and illumination device, respectively, for use with the Safety-stop trochar device and system.

FIG. 17 is a detailed, cut-away view of the safety-stop trochar device and system with a drainage tube attached.

FIGS. 18A and 18B are detailed perspective views of inserts for use with the safety-stop trochar device and system.

FIG. 19 is a detailed perspective view of the base of the safety-stop trochar device and system.

DETAILED DESCRIPTION

Figure 1:
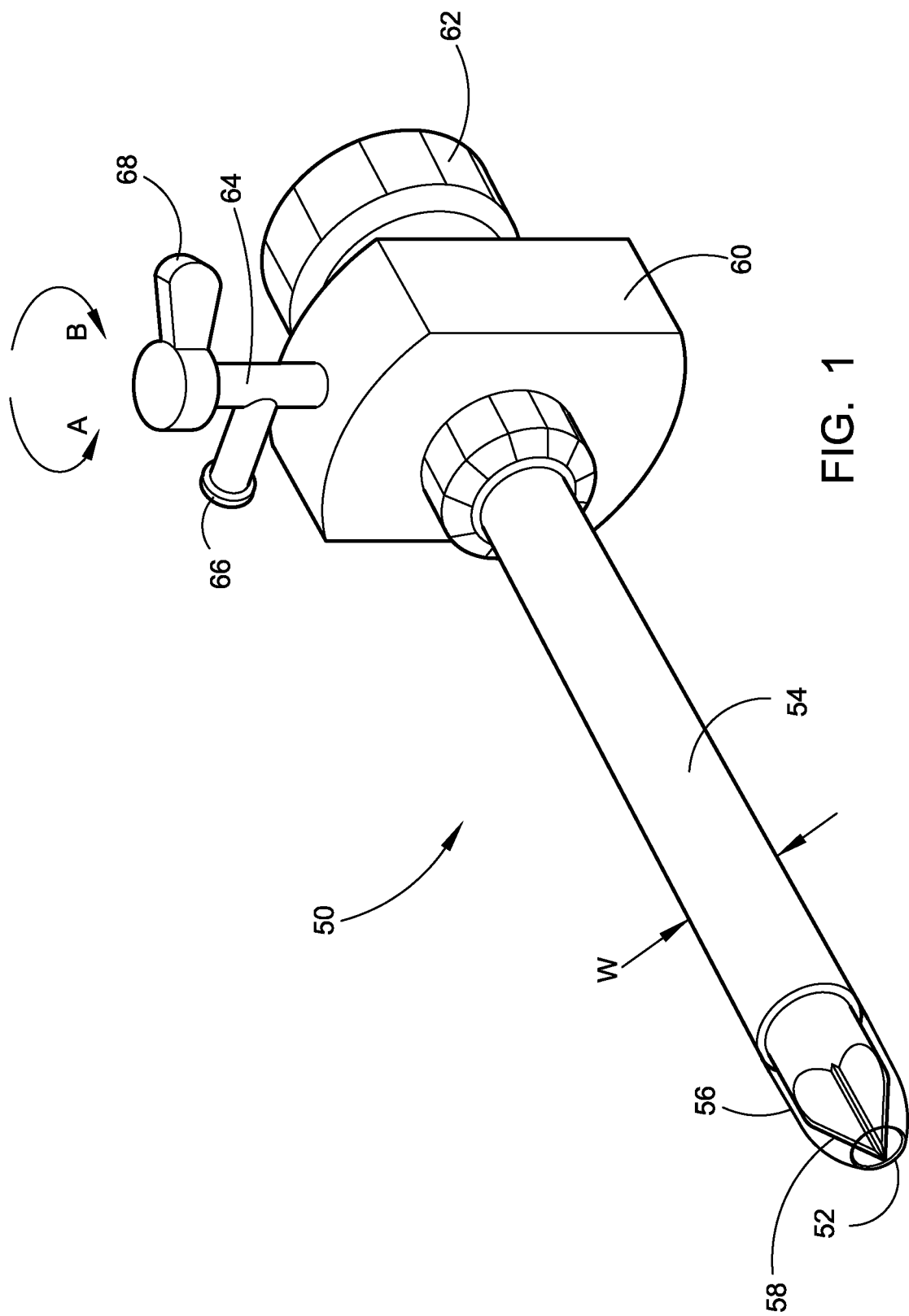
FIG. 1 is perspective view of a typical trochar assembly.

Referring now to the drawings in detail and for a more complete understanding of the safety-stop trochar device and system of the present invention, reference is hereby made to our prior co-pending applications as they relate to FIGS. 1-11. In this regard, and in particular to FIG. 1, a typical trochar assembly 50 is illustrated. Reference character 10 of FIG. 2 which generally designates a safety-stop device of a co-pending application constructed in accordance with a preferred embodiment thereof.

The trochar assembly 50 has a set of blades 58 attached to a knob 62 which, after the trochar assembly 50 is used, is removable from the cannula 54 [trochar tube]. The cannula 54, having a width W, is attached to a head assembly 60 with its components [reference characters 64, 66, 68] thereon. A blade shield 56 with an shield opening 52 at its far end covers the blades 58 to facilitate safe handling of the trochar assembly 50 and to prevent accidental cuttings.

Typically once the trochar assembly 50 has been used to execute the surgical procedure, the surgeon grasps the knob 62 and pulls the blades 58 with blade shield 56 out from the cannula 54. The cannula 54 remains and is in communication with the body cavity into which the trochar assembly 50 penetrated. Suitable hoses [not shown], for example, are connected to the inlet/outlet 66 on valve 64, and the valve lever 68 is positioned on/off [arrows A, B] to, for example, force air or gas into the patient as, and if, necessary to the procedure.

The safety-stop device 10 has a base component 12, an insert component 40, and a cap component 30. The base 12 has a stem 13 [upstanding member] attached thereto and a base channel 14 which is bore completely therethrough from the bottom [point Z1] of the base to and out of the top of the upstanding member 13 [point Z3].

The width of the channel 14 at the bottom of the base is X3-Y3. The width at the opening on the top of the upstanding member 13 is X5-Y5. Width X5-Y5 is greater than width X3-Y3 in that the channel 14 initiates an outward angling 14' above the bottom of the base 14 at approximately point Z2 which bears a width X7-Y7 and terminates at the top [point Z3] of the upstanding member 13 defining an opening thereat having width X5-Y5 wherein width X5-Y5 is greater than width X7-Y7 and wherein width X7-Y7 could be equal to or greater than width X3-Y3. The width of the base 12 [X9-Y9] is substantially greater than the width of the upstanding member 13 [X8-Y8]. It is this base width [X9-Y9] which functions as a stop. The external surface of upstanding member 13 is threaded.

The insert 40, a collet-like component, is configured to fit and seat into the base channel 14, 14' at approximately point Z2 with its exterior surface 44' bearing an angle approximately equal to angle 14'. In this regard, the insert 40 has a height [Z2' to Z3'] which is slightly larger than the distance from point Z2 to point Z3. The insert 40 has a bore 44 vertically disposed therethrough [insert channel]. The width of the insert channel 44 is X2-Y2. The width of the top of the insert 40 is X4-Y4 and the width at the bottom of the insert 40 is X6-Y6. As the insert 40 is structured to seat into the base channel 14, width X4-Y4 is slightly greater than width X5-Y5, and width X6-Y6 is slightly greater than width X7-Y7.

As illustrated in FIGS. 2 and 4, the insert 40 may have one or more vertical slots 46A on the bottom [FIG. 2] or one or more vertical slots 46B, 46D on the top or any combinations thereof. The slots may be extend upward or downward, respectively, partially or, as illustrated in FIG. 5A and 5B, vertically extend the full distance from top to bottom [reference character 46C].

The cap 30 has a hollow interior with threading 38 on the interior surface thereof. The interior threading [female threading] 38 of the cap 30 corresponds with the exterior threading 18 [male threading] of the upstanding member 13. Once the insert 40 is seated into the upstanding member 13 and the cap 30 threaded over the upstanding member 13 a sealing, retaining, and registering unit is formed. On the top of the cap 30 is a cap aperture 34 which has a width X1-Y1.

In this embodiment widths X1-Y1, X2-Y2, X3-Y3 are approximately equal and each are approximately equal to or slightly greater than the trochar tube 56, width W. In operation, there are many methods of attaching the safety-stop device 10 to the trochar assembly 50; i.e., whether the trochar assembly 50 is inserted into the safety-stop device 10 after the safety-stop device 10 has been assembled as a unit or before such assembly as a unit, or whether the assembled or unassembled safety-stop device 10 is inserted onto the trochar assembly 50, or any combinations there.

The final configuration will have the cap 30 distal from the shield opening 52 with the threaded interior 38 facing the shield opening 52. Next is the insert 40, wider end first, followed by the base 12 with its bottom facing the shield opening 52. The insert 40 is seated into the upstanding member 13 and the cap 30 and the upstanding member 13 are connected. In view of the larger size of the insert 40, this connection causes the insert 40 to press against the cannula 54 and tighten and secure around it. The slots 46A, 46B, 46C, depending on which configuration of insert 40 is being used, are squeezed and close or pinch in the process. The tighter the connection between cap 30 and base/upstanding member unit 12, 13, the more securely the safety-stop device 10 is contained on the cannula 54.

Loosening the connection between the base/upstanding member unit 12, 13, loosens the connection between the safety-stop device 10 and the cannula 54 to thereby permit the safety-stop device 10 to translate back and forth on the cannula 54 to any desired point for a pre-determined depth in execution. Once that pre-determined point is established, the safety-stop device 10 is secured to the cannula 54, the trochar assembly is ready to use, and the base 12 acts as a stop once it contacts the skin of the patient to prevent further penetration into the patient's body cavity.

FIGS. 6-8 illustrate a slightly different safety-stop device 10 configuration without an insert 40. Here the base 12 and upstanding member 13 unit are configured externally basically as described above. In this embodiment the upstanding member 13 has one or more vertically disposed slots 16, no internally angled walls 14', and a width W3-W4 at the top. The cap 30 is basically identical except that is has one or more vertically disposed fins 32 on its exterior surface to aid the user in tightening the cap 30 onto the base/upstanding member unit 12, 13. The threading 38 on the inside surface is somewhat tapered in that the width W1-W2 at the top is less than width W3-W4 at the top of the upstanding member 13.

The cap aperture 34 has a width X1-Y1 and the channel aperture 14 at the bottom of the base 12 has a width X3-Y3. Each of these widths [X1-Y1 and X3-Y3] are equal to or slightly greater than the trochar tube 54 width W.

As before, once the safety-stop device 10 and the trochar assembly 50 are attached, tightening the cap 34 over the upstanding member 13, with its smaller width W1-W2, squeezes the upstanding member 13 tightly [in the directions of Arrows D] over the trochar tube 54. Loosening the cap 34 permits the user to slide the safety-stop device 10 to any desired location on the trochar tube 54, re-tighten the cap, and use the trochar assembly 50.

A third embodiment of the safety-stop-device 110 as described in my co-pending applications is illustrated in FIG. 9. Here the upstanding member 13 on the base 13 is not threaded. It has one or more vertically disposed slots 16 and may, but need not, have a collar 22 at the top of the upstanding member 13 to aid in retaining the clamp 20. In operation, the clamp 20 generally is first placed on the trochar tube 54 followed by the base/upstanding member unit 12, 13 through the base channel 14.

Once the unit 12, 13 is slid on the trochar tube 54 where desired, the clamp 20 is placed over the upstanding member 13 and secured thereover. Any suitable clamping device will suffice. As illustrated in FIG. 9, an over-center clamp 20, with lever 24, is utilized because of its ease of use to lock and unlock the clamp 20. Simply moving the lever 24 in the direction of Arrow C tightens the clamp 20 over the upstanding member 13, and squeezes the upstanding member 13 tightly on the trochar tube 54. The slots 16 in the upstanding member 13 cause the upstanding member 13 to be more flexible and, with the pressure of the clamp 20, cause the upstanding member 13, as with the slots described in the previous embodiment, to tightly hold the trochar tube 54.

The base 12 in any embodiment may be round, as illustrated in FIG. 9, or may have one or more side wings, as illustrated in FIG. 8, or may bear any geometric shape suitable for the intended purpose; i.e., to be a stop member. The safety-stop device 10 may be made of any suitable materials, including, but not limited to plastics.

A variation to the first preferred embodiment described above and in my co-pending applications relative to FIGS. 2-5 [with insert 40] and FIGS. 6-8 [without insert 40] is currently illustrated in FIGS. 10 and 11. The basic structures described above, components, and functions are typically the same for this safety-stop device 210 with the difference being the plurality of wings 212 comprising the base component as opposed to the relatively oval base component of FIG. 8 or relatively round base component of FIG. 9.

FIG. 10 illustrates this safety-stop device 210 on the cannula 54 with its upstanding threaded member 13 exposed; i.e., without the cap 30 thereon. Though so illustrated, this safety-stop device 210, as mentioned above, does have the same components as the other embodiments and functions in the same manner. FIGS. 10 and 11 illustrate 3 wings 212 forming the base component, though there could be more. Three however have been found to accord the stability envisioned of this type base component and its functionality.

The wings 212 generally are equally spaced around the axis of the base component. In this regard, where the base component has three such wings 212, they are spaced approximately 120° apart from each other. Where the base component has four such wings 212, for example, they are spaced approximately 90° apart from each other.

As described above, once the trochar has penetrated the body and the cannula 54 inserted a passage has been formed by way of the cannula 54 for insertion and use of various surgical implements. For this purpose, the cannula 54 must be held steady with minimal, or preferably, no movement. The base component structures being relatively oval or round, though suited for the intended purpose, do not accord maximum stability.

It has been found that a base component with three or more wing structures 212 accord greater stability of use. Moreover, the apertures 214 adjacent to the ends of the wings 212 accord the user even greater stability. With the safety-stop device 210 held firmly in place, a user sutures the base component to the patient through the apertures 214. Once the base component is secured to the patient, the user or the user's assistant is not required to manually hold the base component firmly against the patient. This thereby frees a hand for additional assistance and further provides for an extremely secured attachment.

It has been found that a thermoplastic material or a thermoplastic rubber material is best suited for the construction of the base 12, 212 and the wings in any embodiment illustrated herein. This construction for the base 12, 212 and wings gives them a greater pliability thereby affording a user greater flexibility for placement and use of the safety-stop device 10, 210. Depending on where a trochar is to be used on a patient, angling of the safety-stop device 10, 210 may be necessitated.

The pliability of the base 12, 212 and wings, due to the materials of which they are composed, facilitate placement, angling, and safe and more exacting use of the safety-stop device 10, 210 and trochar attached to it; particularly in areas which are difficult to access.

FIGS. 12-19 apply to the newly conceived components and structure of this new and entire safety-stop trochar device and system. Key features to this new safety-stop trochar device and system include a smoke evacuator, drainage tube, obturator, dome light illumination, adhesive on the bottom of the base, and U-shaped extensions on the cap to be now described in detail.

FIG. 12 illustrates the 212, as described above, with the addition of the adhesive material 219 on the underside thereof. This form of base 210 with wings 212 and adhesive 219 is designed to allow the surgeon a variety of methods to stabilize the safety-stop trochar device/system at right angles to the body through the use of any form of adhesive suited for the intended purpose, such as, but not limited to double sided adhesive attached to the underside It should have a releasable liner in the event the surgeon elects not to use it at all and may have a split releasable liner so the surgeon can "change his mind" and use the adhesive after he has the base 210 on the trochar. The adhesive backed wings 212 can actually be made of an adhesive material or made of a durable, yet pliable, double sided tape, die cut to fit the base 210 with a releasable liner attached thereto. This feature provides a secure base to which the safety-stop trochar device/system can be attached to the skin of the patient during laparoscopic surgery.

Figure 14:
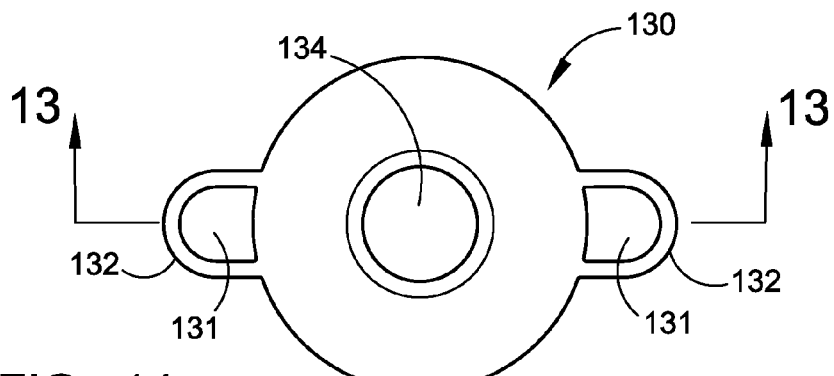
FIG. 14 is a top plan view of the cap of the new safety-stop device illustrating in detail the U-shaped extensions.
Figure 13:
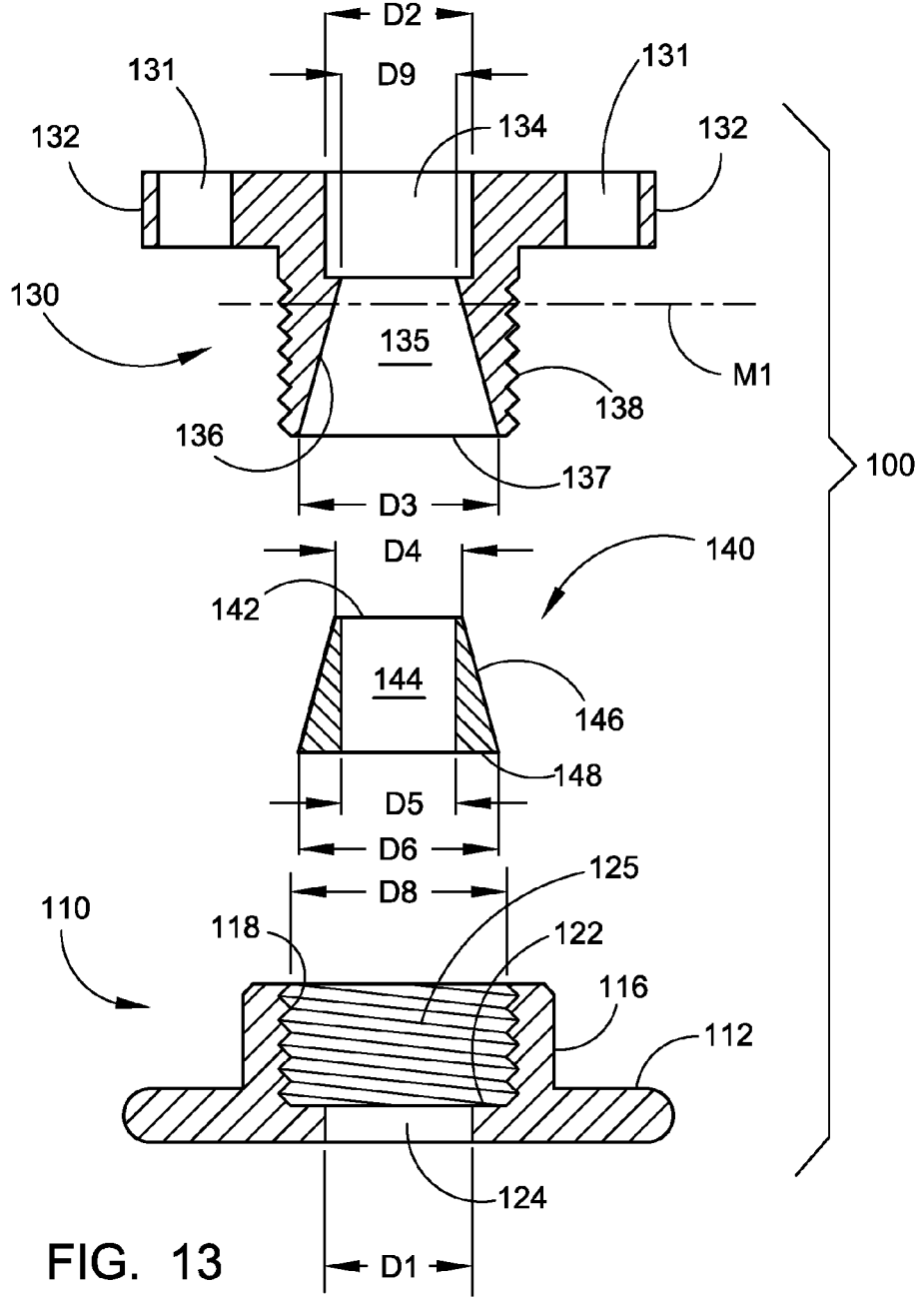
FIG. 13, as taken on line 13-13 of FIG. 14, is an exploded cut-away view of the new safety-stop device.

FIGS. 13-15 illustrate the preferred embodiment of the safety-stop trochar device/system 100 of the present invention. The base 110 is not unlike the base 212 previously described having three flexible extension wings 112 extending axially outward, suture apertures 114 in the extension wings 112, and an opening 124 in the floor 122. The upstanding member 116 is internally threaded 118 and its inner chamber is substantially perpendicular to the extension wings 112 and the floor 122 within the inner chamber.

For reference purposes, the floor opening 122 has a diameter-D1 and the inner chamber 125 has a diameter-D8. The insert 140 of this entire system 100 has a bottom 148 which is wider than its top 142 with an angled side wall 146 angling downward and outward as seen in detail in FIG. 13. As with my co-pending applications, this insert 140 also has a central bore 144 therethrough from top 142 to bottom 148 and is made of a flexible or pliable material to permit its compression when the cap 130 is threaded onto the base 110 with the insert 140 seated therein.

For reference purposes, the top 142 has a diameter-D4, the bore 144 has a diameter-D5, and the bottom 148 has a diameter-D6 and diameter-D6 is equal to or less than diameter-D8. As such, the bottom 148 will rest on the floor 122 when the insert 140 is placed into the inner chamber 125 of the base 110 and the top 142 may be co-planar with the top of the upstanding member 118 or below that top. Diameter-D4 is approximately equal to diameter-D1.

The cap 130 has been modified from the cap of the co-pending applications by the addition of U-shaped extensions 132 to the basic design of the which then allows the surgeon to attach the device to the trochar without the use of an external implement such as a wrench or pliers. This feature also allows easier tightening and loosening of the device around the trochar and facilitates adjusting intra-operatively, if indicated. It is unobtrusive, easy to manufacture and use, and eliminates the need for an extra part that can be misplaced.

The U-shaped extensions 132 are generally on opposing sides and adjacent to the top of the cap 130. As so structured, an opening 131 is defined with the U-shaped extensions 132. It has been found that such extensions 132, on opposing sides, and protruding outward substantially will greatly aid the user in fastening and unfastening the cap 130 to and from the base 110; all without the need of an external tool or device. It has also been found that structuring the extensions 132 as U-shaped with the openings 131 makes the extensions 132 stronger, more durable, and facilitates manufacture.

The cap outer wall 138, extending substantially downward from its top and U-shaped extensions 132, is threaded. An opening through the cap from top to bottom consists of two distinct sections; an upper section opening 134 which is perpendicular to the cap bottom 137 [and when threaded into the base 110 is perpendicular to the floor 122] and a lower section opening 135 with a top diameter, diameter-D9, and a bottom diameter, diameter-D3, wherein the bottom diameter is greater than the top diameter. As such its inner wall 136 is angled downward and outward toward the cap bottom 137 defining a bottom ring. The angled inner wall 136 bears an angle which is approximately equal to the angled side wall 146 of the insert 140. This configuration facilitates acceptance of the insert 140 and, due to its flexible characteristics and pliability, its compression to thereby secure external objects within the insert bore 144.

The cap 130 height has a mid-point designated as M1 in FIG. 13. The upper section opening 134 extends downward to a point above the cap mid-point M1 and has a diameter-D2 wherein diameter-D2 is approximately equal to diameter-D1 but generally greater than diameter-D5.

The angled lower section opening 135 is defined and begins with the top diameter of it as being adjacent to and immediately below the upper section opening 134 at a point above the cap mid-point M1. This top diameter, diameter-D9, may be equal to or less than diameter-D2 [for illustration purposes only diameter-D9 is shown to be less than diameter-D2]. The angled inner wall 136 of the lower section opening 135 is angled downward and outward bearing approximately the same angle as the side wall 146 of the insert 140.

The cap 130 is externally threaded 138 from below the extensions 132 downward to the bottom ring at the cap bottom 137. This external threading 118 corresponds to the internal threading 118 of the base 110. The opening in the bottom ring at the cap bottom 137, the bottom diameter of lower section opening 135, diameter-D3, is approximately equal to diameter-D6 on the bottom 148 of the insert 140 and is greater than diameter-D9.

This structure is completely different than that of my co-pending applications as to the U-shaped extensions 132 on the cap 130, threading locations, inverted insert 140, and lower section opening 135 of the cap 130 angled relatively correspondingly to the angling of the insert. This structure of inverted insert 140 and angled lower section opening 135, with an external device therein [such as a trochar or other relatively circular external object], provides greater securing power of the external device. As with the devices of my co-pending applications, the insert 140 compresses onto the external device as the cap 130 is attached and threaded into the base 110.

A truly unique and novel feature of the safety-stop trochar device/system is further illustrated in FIGS. 15-19. FIGS. 15 and 19 illustrate the base of this system as described above. The extension wings 112 should be relatively flexible and pliant with the underside having an adhesive 119 in addition to or in lieu of the suture apertures.

The insert 140A as shown in FIGS. 18A and 18B has a plurality of upper downward descending slots 146D [top slots] and a plurality of lower upward ascending slots 146A [bottom slots]. Four top slots 146D, equally spaced apart and four bottom slots 146A, also equally spaced apart and in between the top slots 146D are the preferred embodiment of this insert 140A.

In FIG. 18B the slots 146A, 146D go up and down, respectively, approximately one-half the distance of the length of the side wall 146, In FIG. 18A, the slots go up and down, respectively, greater than one-half the distance of the length of the side wall 146. The insert 140 as previously described may also be similarly configured of may be without top slots 146D or bottom slots 146A.

It is preferred that the top slots 146D are cut relatively perpendicular to the top 142 and run downward approximately one-half the distance of the length of the side wall 146 and the bottom slots 146A also cut relatively perpendicular to the bottom 1148 and run upward approximately one-half the distance of the length of the side wall 146.

Two significant features of this safety-stop trochar device/system include the smoke evacuator and drainage device each to be used in conjunction with the base 110, insert 140 or 140A, and cap as described above independently and in place of the trochar. FIG. 17 is illustrative of such use with reference character 154, a flexible or rigid tube or conduit, as partially symbolizing either the smoke evacuator or the drainage device inserted through the insert 140 and compressed by the insert 140 between the base 110 and the cap 130 and is described in greater detail below.

Any conventional smoke evacuator or drainage device suited for the intended purpose for surgical assistance will suffice. A typical smoke evacuator consists of a hollow tube or rigid conduit of approximately between 4-6 millimeters in communication with the peritoneal cavity at one end [inside end] and connected at its outside end to a conventional suction or vacuum machine with an on-off switch or button to activate the machine to thereby remove the smoke being generated.

In practice what is envisioned is placing a rigid or flexible conduit into the insert bore 144 and down past the floor opening 124 and then fastening the cap 130 onto the base 110. Generally a flexible hose is then attached to the conduit at one end and to a conventional a suction machine or vacuum machine.

If a only a flexible hose is used, then the inside end is placed into the peritoneal cavity as described above and the other, outside end, is attached to the conventional suction machine or vacuum machine. The diameter of a tube or conduit as described above generally should be approximately equal to diameter-D5.

The purpose of a drainage device is to remove accumulating blood or pus, which accumulates over a period of time, generally from 1 to 4 days. These drainage devices generally are sutured to the skin, which is NOT ideal when infection and pus are present, as is often the case. Our safety-stop device and entire new system 100, with the adhesive base 119, can secure the drainage devices more optimally and provides a secure base to which a drainage tube can be attached. It requires only that the safety-stop trochar device/system be provided with one 1-2 additional inserts 140, 140A with a bore 144 of comparable diameter to fit the common sizes of the various drainage devices.

In practice what is envisioned is placing a rigid or flexible conduit into the insert bore 144 and down past the floor opening 124 and then fastening the cap 130 onto the base 110. Generally a flexible hose is then attached to the conduit at one end and to a conventional a suction machine, vacuum machine, irrigating device or manually operated suction bulb.

If a only a flexible hose is used, then one end [inside end] is placed into the peritoneal cavity as described above and the other, outside end, is attached to a conventional a suction machine, vacuum machine, irrigating device or manually operated suction bulb. The diameter of a tube or conduit as described above generally should be approximately equal to diameter-D5.

As previously described, the current method of attaching a drainage devices is insecure and often un-sterile and can be accidentally pulled out. Many complications occur because sutures have to be placed in an area of the body that may be contaminated by pus. For aesthetic reasons, many patients find suture scars undesirable. The adhesive back 119 of the safety-stop trochar device/system base 110 provides a secure platform for inserting the drainage device and eliminates the need for stitches when holding it in place. Our original safety-stop device, in itself is a unique device and the drainage device was designed to supplement it, as a complete system in a way that makes it even more unique in it's design and overall function.

The inclusion of an illumination device and an obturator fill out this new and improved complete safety-stop trochar device/system. The illumination device provides a method by which a light can be inserted into the peritoneal cavity after a trochar incision. The device can be corded or non corded (battery powered) and can be positioned exactly where the surgeon desires all without impeding other trochar entries and eliminates the need for an extra set of hands to position the base or trochar or laparoscope lighting system for better placement of laparoscopic surgical instruments. It does not impede performance of the remainder of the surgery and can illuminate the entire peritoneal operating field.

Typical illumination devices suited for the intended purpose include, but are not limited to a fiber optic cable hooked up to a laparoscope using alternating current to power the light.

The inclusion of an obturator provides a method by which a trochar entry can be maintained safely. The obturator can be inserted into the peritoneal cavity with relative ease and as unintrusively as possible. It can be made of any plastic, thermoplastic, rubber, metal, urethane or polymer and can be installed in less than a minute permitting easy entry for the surgeon to place a scope for a second look and obviates the need for stitching and un-stitching the incision which is partially healed. It does not impede performance of the remainder of the surgery.

Reference is made to FIGS. 15, 16A, and 16B. With the use of miscellaneous surgical accessories, such as, but not limited to, the illumination device 160B and an obturator 160A, there is no need for the insert 140. Each device 160A, 160B has a relatively flat, circular platform 162 with a diameter-D7 and descending downward from the platform 162 are extension members, symbolizing either the illumination device by reference character 160B or the obturator by reference character 160A This extension member, and respective devices 160A, 160B, each have a diameter-D10 wherein diameter-D10 is equal to or less than diameter-D1 and diameter-D7 is equal to or less than diameter-D8 but greater than diameter-D1 and is greater than diameter-D3. The extension member may be rigid or flexible and should, but need not, have a rounded surface at its distal end. For the illumination device 160B, a powered light is at the distal end. The powered light may be, but is not limited to, an LED light or any conventional fiber optic light, suitable to illuminate the peritoneal cavity into which inserted. The power source may be internal to the device or external to the device and, in either case, have a control for on-off operations.

The respective device [illumination device 160B or obturator 160A] is first inserted into the base 110 through the opening in the floor 122. The platform 162, having a larger diameter [diameter-D7] than the opening in the floor [diameter-D1], rests on the floor 122.

The cap 130 is threaded into the base 110. With the cap bottom 137 opening having a diameter [diameter-D3] which is less than the diameter of the platform 162 [diameter-D7], the floor 137 is tightened down and onto the platform 162 thereby securing the respective device [illumination device 160B or obturator 160A] therein.

The present disclosure includes that contained in the present claims as well as that of the foregoing description. Although this safety-stop trochar device and system has been described in its preferred forms with a certain degree of particularity, it is understood that the present disclosure of the preferred forms has been made only by way of example and numerous changes in the details of construction and combination and arrangement of parts and method steps may be resorted to without departing from the spirit and scope of the safety-stop trochar device and system. Accordingly, the scope of the safety-stop trochar device and system should be determined not by the embodiments illustrated, but by the appended claims and their legal equivalents.

What is claimed is:

1. A safety-stop trochar device and system comprising:
   (a) a base having a bottom and a circular upstanding member with an internally threaded inner chamber and a floor therein having a diameter-D8, an opening through said floor having a diameter-D1 wherein said diameter-D8 is greater than said diameter-Dl, and at least three non-rigid extension wings extending axially outward from said base adjacent to, and aligned with, said floor;
   (b) a cap defined by a bottom end, a top end, and with a mid-point relative to said bottom and top ends, said cap having an opening through said top end comprising a upper section opening with a diameter-D2, said diameter D2 extending downwardly to a point above said mid-point and being approximately perpendicular to said floor and a lower section opening adjacent to and below said upper section opening wherein said lower section opening has a top diameter, diameter-D9, and a bottom diameter, diameter-D3, wherein said diameter-D3 is greater than said diameter-D9 and greater than said diameter-D2 and wherein said diameter-D9 is approximately equal to or less than said diameter-D2, said cap further having external threading which corresponds to said internally threaded inner chamber of said circular upstanding member; and
   (c) an insert adapted to seat onto said floor, said insert having a top with a diameter-D4 and a bottom with a diameter-D6 wherein said diameter-D6 is greater than said diameter-D4 and is approximately equal to or less than said diameter-D8 but greater than said diameter-D1 thereby defining a downward and outward angled side wall, said insert further comprising a bore therethrough having a diameter-D5 wherein said diameter-D5 is less than said diameter-D4 and is approximately equal to or less than said diameter-D1.

2. The safety-stop trochar device and system of claim 1 further comprising at least two U-shaped extensions on said cap above said mid-point.

3. The safety-stop trochar device and system of claim 1 further comprising an adhesive on the bottom of said base.

4. The safety-stop trochar device and system of claim 1 further comprising an aperture on each of said at least three extension wings at their respective distal ends.

5. The safety-stop trochar device and system of claim 1 wherein said at least three extension wings are sufficiently flexible to reduce patient bruising when said wings are attached to said patient's skin.

6. The safety-stop trochar device and system of claim 1 further comprising an elongated conduit having a first end and a second end wherein said first end inserts through said cap opening, through said insert bore, and through said base floor opening into the peritoneal cavity and said second end is connected to an external object selected from the group consisting of smoke evacuators and drainage devices.

7. A safety-stop trochar device and system comprising:
   (a) a base having a bottom and a circular upstanding member with an internally threaded inner chamber and a floor therein having a diameter-D8, an opening through said floor having a diameter-D1 wherein said diameter-D8 is greater than said diameter-Dl, and at least three non-rigid extension wings extending axially outward from said base bottom;
   (b) a cap with a mid-point relative to its height, said cap having an opening therethrough comprising a upper section opening with a diameter-D2 and being approximately perpendicular to said floor and a lower section opening adjacent to and below said upper section opening wherein said lower section opening has a top diameter, diameter-D9, and a bottom diameter, diameter-D3, wherein said diameter-D3 is greater than said diameter-D9 and greater than said diameter-D2 and wherein said diameter-D9 is approximately equal to or less than said diameter-D2, said cap defining an upper bore section having a cylindrical shape defined by diameter D2 and a lower bore section having an upwardly-turned conical shape defined by diameter D9 at its upper end and by diameter D3 at its lower end, said cap further having external threading which corresponds to said internally threaded inner chamber of said circular upstanding member; and
   (c) surgical accessory means for placement into and past said base into a patient's peritoneal cavity and secured in said base by said cap for assisting a surgeon in a surgical procedure in the peritoneal cavity, said surgical accessory means comprising an [unitary]outer housing defined by a platform having a diameter-D7 and an extension member extending downward from said platform having a diameter-D10, wherein said diameter-D7 is approximately equal to or less than said diameter-D8 and is greater than said diameter-D3 and said diameter-D10 is approximately equal to or less than diameter-D1.

8. The safety-stop trochar device and system of claim 7 wherein said extension member comprises a tube with a rounded distal end.

9. The safety-stop trochar device and system of claim 7 wherein said rounded distal end further comprises a powered illumination device.

10. The safety-stop trochar device and system of claim 7 wherein said extension member is made of a rigid material.

11. The safety-stop trochar device and system of claim 7 wherein said extension member is made of a flexible material.

12. A safety-stop for trochar devices, comprising:
   (a) a base having a bottom and a circular upstanding member with an internally threaded inner chamber defined by a floor having a central aperture formed therethrough, and at least three non-rigid extension wings extending axially outward from said base bottom, said extension wings defining a bottom face opposite a top face, and further comprising adhesive material covering said bottom face;

(b) a cap with a mid-point relative to its height, said cap having an opening therethrough comprising a upper section opening and a lower section opening adjacent to and below said upper section opening wherein when said cap is threadedly engaging said base internal threads, said upper section opening, said lower section opening and said central aperture are in relative juxtaposed position said cap further defining an upper bore section having a cylindrical shape defined by diameter D2 and a lower bore section having an upwardly-turned conical shape defined by diameter D9 at its upper end and by diameter D3 at its lower end, said cylindrical upper bore section terminating above said mid-point; and (c) an insert adapted to seat entirely within said chamber, said insert defining a generally conical outer wall and a cylindrical inner bore, and having opposing top and bottom ends, the relative separation of said ends defining a height of said insert, said insert further defined by a plurality of slots formed at said top and bottom ends, with said slots in said top end in radial spaced relation as compared to said slots in said bottom end, with each said slot defining a depth that is less than said insert height.

* * * * *